(12) United States Patent
Schuessler

(10) Patent No.: US 8,609,004 B2
(45) Date of Patent: Dec. 17, 2013

(54) METHOD OF FORMATION OF A MEDICAL IMPLANT

(75) Inventor: David J. Schuessler, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 10 days.

(21) Appl. No.: 13/288,885

(22) Filed: Nov. 3, 2011

(65) Prior Publication Data

US 2012/0139157 A1 Jun. 7, 2012

Related U.S. Application Data

(62) Division of application No. 12/431,070, filed on Apr. 28, 2009, now Pat. No. 8,070,809.

(60) Provisional application No. 61/038,919, filed on Apr. 28, 2008.

(51) Int. Cl.
*B29C 41/04* (2006.01)
*B29C 41/20* (2006.01)

(52) U.S. Cl.
USPC .......................................... 264/275; 264/310

(58) Field of Classification Search
None
See application file for complete search history.

(56) References Cited

U.S. PATENT DOCUMENTS

| | | | | |
|---|---|---|---|---|
| 3,204,959 A | * | 9/1965 | Nicholls | ........................ 473/610 |
| 3,301,254 A | | 1/1967 | Schickedanz | |
| 3,852,832 A | | 12/1974 | McGhan | |
| 4,332,634 A | * | 6/1982 | Aperavich | ..................... 156/145 |
| 4,605,412 A | | 8/1986 | LaForest et al. | |
| 4,636,213 A | * | 1/1987 | Pakiam | ............................. 623/8 |
| 4,773,909 A | | 9/1988 | Chaglassian | |
| 5,019,101 A | | 5/1991 | Purkait et al. | |
| 5,022,942 A | | 6/1991 | Yan et al. | |
| 5,084,061 A | | 1/1992 | Gau et al. | |
| 5,171,269 A | | 12/1992 | Bark | |
| 5,447,535 A | | 9/1995 | Muller | |
| 5,456,716 A | | 10/1995 | Iversen | |
| 5,674,285 A | | 10/1997 | Quaid | |
| 5,895,423 A | | 4/1999 | Becker et al. | |
| 6,074,421 A | * | 6/2000 | Murphy | ............................ 623/8 |
| 6,228,116 B1 | | 5/2001 | Ledergerber | |
| 6,602,452 B2 | | 8/2003 | Schuessler | |
| 6,692,527 B1 | | 2/2004 | Bellin et al. | |
| 6,733,512 B2 | * | 5/2004 | McGhan | ....................... 606/192 |
| 6,955,690 B1 | * | 10/2005 | Cao | ..................................... 623/7 |
| 8,070,809 B2 | | 12/2011 | Schuessler | |
| 2003/0149481 A1 | | 8/2003 | Guest | |
| 2003/0171768 A1 | * | 9/2003 | McGhan | ....................... 606/191 |
| 2007/0198085 A1 | | 8/2007 | Benslimane | |
| 2009/0012372 A1 | | 1/2009 | Burnett et al. | |
| 2009/0030515 A1 | | 1/2009 | Schuessler et al. | |
| 2009/0198332 A1 | | 8/2009 | Becker | |
| 2009/0198333 A1 | | 8/2009 | Becker | |
| 2009/0202608 A1 | | 8/2009 | Alessi et al. | |
| 2009/0270985 A1 | | 10/2009 | Schuessler | |
| 2009/0275974 A1 | | 11/2009 | Marchand et al. | |
| 2010/0070042 A1 | | 3/2010 | Bryan et al. | |
| 2010/0168853 A1 | | 7/2010 | Job | |
| 2012/0197393 A1 | * | 8/2012 | Yu | ..................................... 623/8 |

FOREIGN PATENT DOCUMENTS

| | | | |
|---|---|---|---|
| EP | 0872221 | * | 10/1998 |
| WO | 2010022130 | | 2/2010 |

* cited by examiner

*Primary Examiner* — Edmund H. Lee
(74) *Attorney, Agent, or Firm* — Linda Fox; Debra Condino

(57) ABSTRACT

An elastomeric prosthetic breast implant is provided having a shell and a patch forming a flush interface with the shell and no sudden surface steps on both interior and exterior surfaces of the shell.

4 Claims, 6 Drawing Sheets

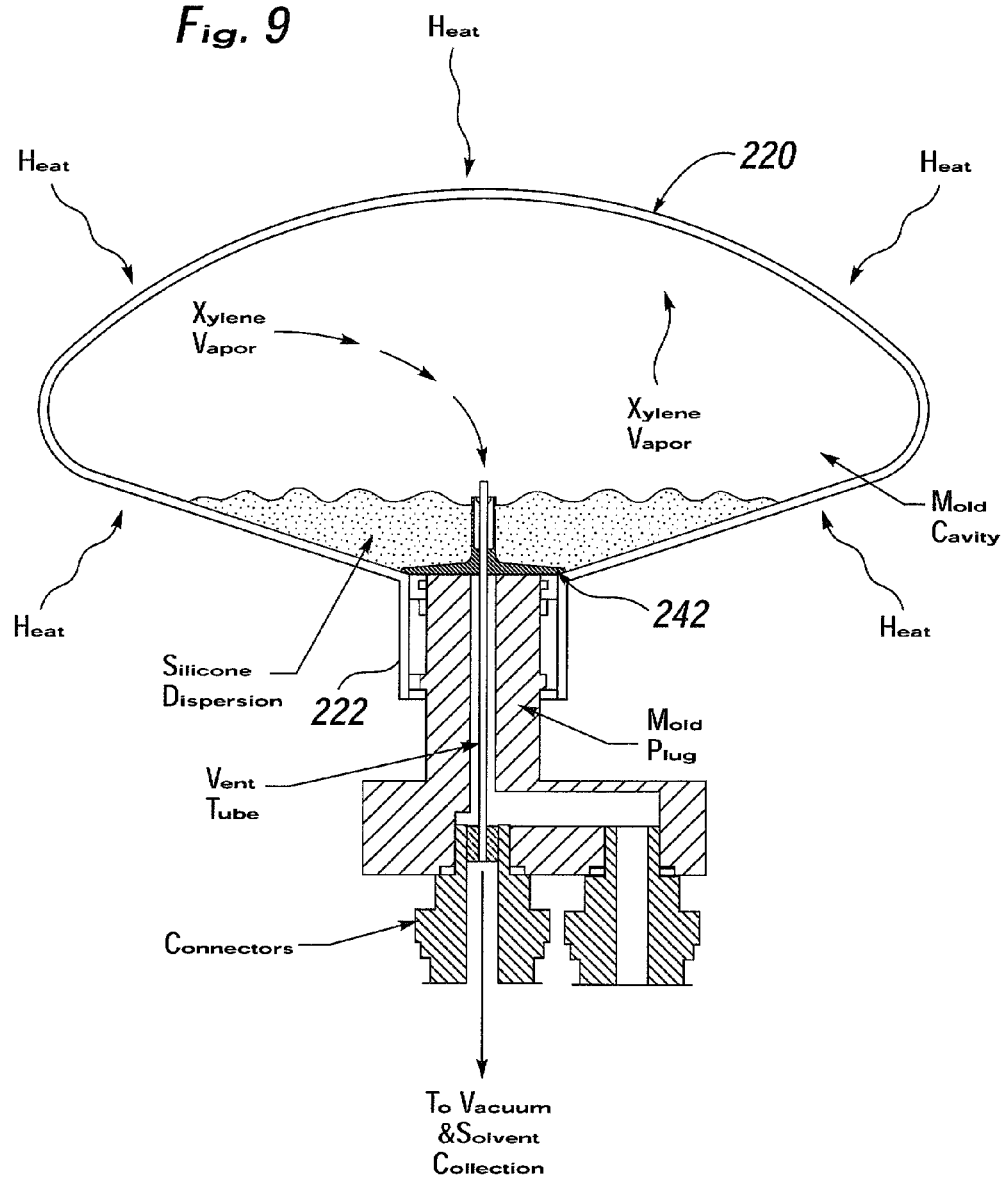

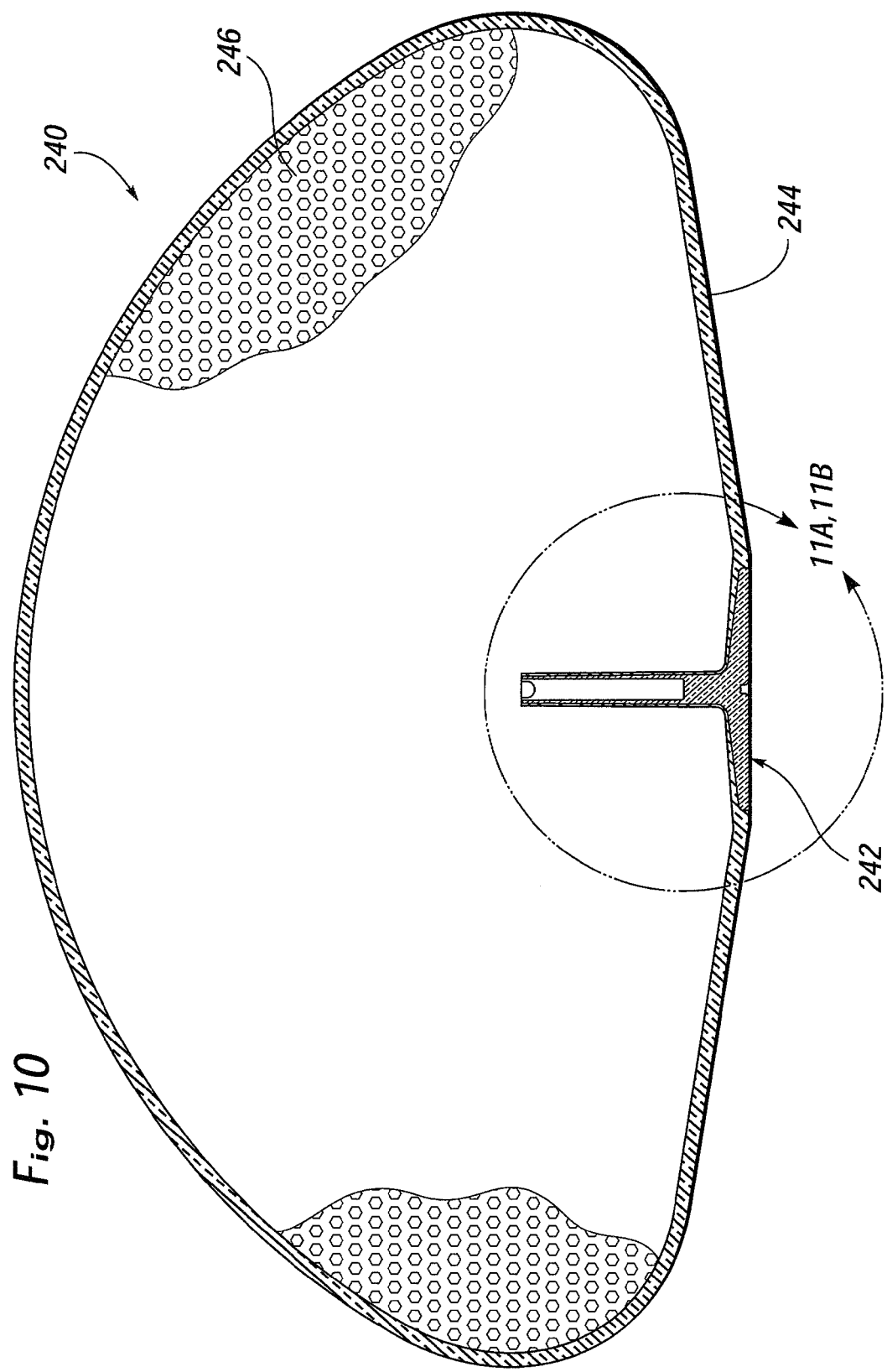

METHOD OF FORMATION OF A MEDICAL IMPLANT

RELATED APPLICATION

This application is a divisional of U.S. patent application Ser. No. 12/431,070, filed Apr. 28, 2009, which claims the benefit of U.S. Provisional Patent Application No. 61/038,919, filed on Apr. 28, 2008, the entire disclosure of which is incorporated herein by this specific reference.

FIELD OF THE INVENTION

The present invention relates to patches for elastomeric implants and, more particularly, to devices and methods for forming a patch flush with an elastomeric implant shell.

BACKGROUND OF THE INVENTION

Implantable prostheses are commonly used to replace or augment body tissue. In the case of breast cancer, it is sometimes necessary to remove some or all of the mammary gland and surrounding tissue that creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and quite flexible envelope or shell made of vulcanized (cured) silicone elastomer. The shell is filled either with a silicone gel or with a normal saline solution. The filling of the shell takes place before or after the shell is inserted through an incision.

One process for forming flexible implant shells for implantable prostheses and tissue expanders involves dipping a suitably shaped mandrel into a silicone elastomer dispersion. The outer silicone elastomer shell may have an anatomical configuration, in this case matching the breast, and comes off the mandrel with a shell hole. A patch over the shell hole typically includes an uncured portion directly over the hole and a cured portion covering that and adhered to the inner surface of the shell. The patch is cured and then the hollow interior of the shell is filled with an appropriate gel via a needle hole in the patch. The needle hole in the patch is then sealed with a silicone adhesive and the implant oven cured to achieve cross-linking of the gel.

Another process for forming implant shells is rotational molding, such as the system and methods described in U.S. Pat. No. 6,602,452 to Schuessler. The process also results in a flexible implant shell having a hole that requires a patch.

Patches for flexible implant shells are sized larger than the manufacturing hole to provide some bonding area. The overlap of the patch on the shell results in a slight surface step on the inside or outside of the shell which may be noticeable in the finished product, which is undesirable. Also, such a palpable step or discontinuity may irritate tissue in contact with the exterior of the implant.

Despite many advances in the construction of soft prosthetic implant shells, there remains a need for a smoother joint between a patch and a manufacturing hole in the implant shell.

SUMMARY OF THE INVENTION

In accordance with the present invention, a hollow medical implant comprises an elastomeric hollow shell having a contiguous and consistent wall except in an access region, and a patch extending thereacross. The patch is securely bonded to the shell and a peripheral edge of the patch and the shell cooperate to form a flush interface with no surface steps on both interior and exterior surfaces of the implant.

In another aspect, the invention includes a hollow medical implant, comprising an elastomeric hollow shell having a contiguous and consistent wall except in an access region. A patch extends across the access region of the shell and securely affixes thereto. The patch has an outer flange and the shell wall forms an exterior butt joint against a peripheral edge of the flange and overlaps an inner surface of the flange in a manner that results in no surface steps.

Both the elastomeric hollow shell and patch may be made of materials with similar elastic modulus, durometer and elongation, and may even be made of the same material. Desirably, the elastomeric hollow shell is made of a solvent-based solid elastomer and the patch is made of a liquid silicone rubber without a solvent. In one embodiment, the patch includes a stem projecting radially inward into the interior of the hollow shell and an outer flange extending circumferentially outward from the stem, wherein the shell wall forms a flush butt joint against a peripheral edge of the flange and overlaps an inner surface of the flange and extends at least to the stem. In another embodiment, the patch is a substantially flat disk shape and the shell wall covers an entire inner face of the patch. The patch flange may increase in radial thickness from its periphery toward its center such that the portion of the shell wall that overlaps the inner surface of the flange is thickest adjacent the flange periphery.

In one form, the implant is for implantation in the breast and the elastomeric hollow shell is accordingly shaped. Other implant applications include for the buttocks, testes, calf, etc. In some embodiments, the implant is a fillable implant, for example, a saline fillable breast implant or tissue expander. In other embodiments, the implant is an intragastric balloon.

In some embodiments, the implant is a fillable or inflatable implant such as a saline finable breast implant or an inflatable intragastric balloon and the patch includes a fill valve for facilitating inflation of the implant.

The present invention also embodies a method of formation of a medical implant, comprising:

providing a mold cavity having a sprue orifice;
covering the sprue orifice with a patch;
introducing a silicone elastomer into the mold cavity;
causing the silicone elastomer to distribute generally evenly around the mold cavity and over at least a portion of the patch;
curing the silicone elastomer to form a hollow implant shell having the patch bonded thereto; and
removing the implant shell from the mold cavity.

The patch may be shaped relative to and positioned within the mold cavity so that after formation of the hollow implant shell a peripheral edge of the patch and the shell cooperate to form a flush interface with no sudden surface steps on both interior and exterior surfaces of the implant. The step of introducing preferably includes introducing the silicone elastomer into the mold cavity through the patch. During the step of causing the silicone elastomer to distribute generally evenly around the mold cavity the method may include extending a vent tube through the patch and venting gas from within the mold cavity though the vent tube. Also, a tube may be inserted through the patch for filling the mold cavity with a silicone gel through the tube, which is then cured to form a solid prosthesis.

BRIEF DESCRIPTION OF THE DRAWINGS

Features and advantages of the present invention will become appreciated as the same become better understood with reference to the specification, claims, and appended drawings wherein:

FIG. 9 is a cross-sectional view through an exemplary mold of the present invention showing various elements of a process for forming a flush patch;

FIG. 10 is a cross-sectional view through an exemplary gel-filled breast implant prosthesis having a molded-in-place flush patch formed in accordance with the present invention;

DETAILED DESCRIPTION OF THE PREFERRED EMBODIMENTS

The present invention provides a gel-filled implant prosthesis incorporating a shell composed partly or entirely of a fluid barrier layer, preferably a silicone elastomer. The implant shells of the present invention may have a single material layer of homogeneous or uniform composition, or a laminated or layered configuration. The primary application for gel-filled soft implants is to reconstruct or augment the female breast. Other potential applications are implants for the buttocks, testes, or calf, among other areas. Moreover, though the present invention is particularly advantageous for gel-filled implants, saline filled breast implants or intragastric balloons may be modified to incorporate the benefits herein. Further, tissue expanders which may not be viewed as implants, per se, may also use the concepts disclosed herein. For that matter, the term implant as used herein refers to long and short-term implanted devices.

The implant shells of the present invention are desirably formed using a rotational molding system, such as disclosed in U.S. Pat. No. 6,602,452 to Schuessler, which is expressly incorporated herein by reference. Schuessler discloses a rotational molding machine for forming medical articles, in particular for molding silicone elastomer shells for breast implants. Molding machines other than those that rotate the mold, such as insert molding machines in general (the insert being the patch), may conceivably be used to mold in place the flush patch as described herein, and the advantages of the present invention may even be incorporated into traditional dip molding method, though modifications to the typical dipping mandrel and rod are necessary and will not be described herein.

The advantage of insert molding the patch in place within the shell is that the patch integrates with the shell. That is, the shell material flows over and around the patch and bonds tightly thereto, if not actually melding together to blur any distinct boundaries between the two items. How much of this integration occurs depends on the similarity in the materials, and the mold process parameters such as time and temperature. Preferably the shell comprises a solvent-based solid elastomer (e.g., silicone) and the patch is formed of a liquid silicone rubber (LSR) without a solvent and with a similar elastic modulus, durometer and elongation as the shell. Similar physical properties permits the patch to deform and stretch with the shell which reduces stress concentrators. Alternatively, the materials of the patch and shell could be identical.

Figure 1:
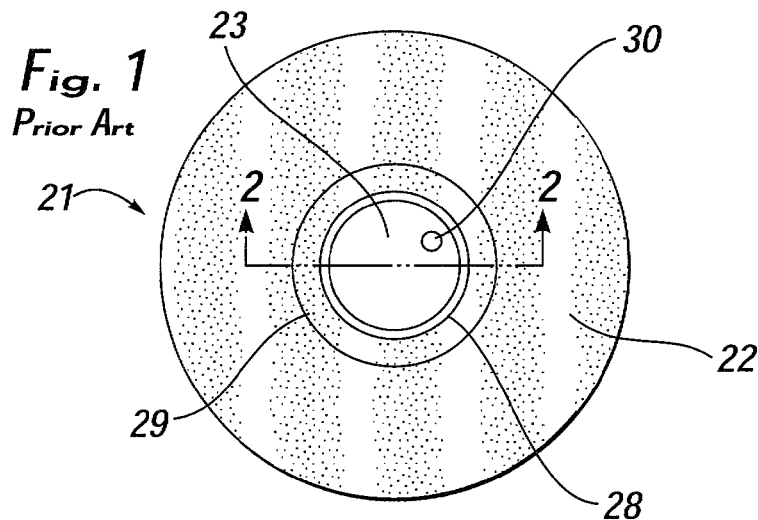
FIG. 1 is a plan view from above of a elastomeric implant sealed by a patch construction in accordance with the prior art.
Figure 2:
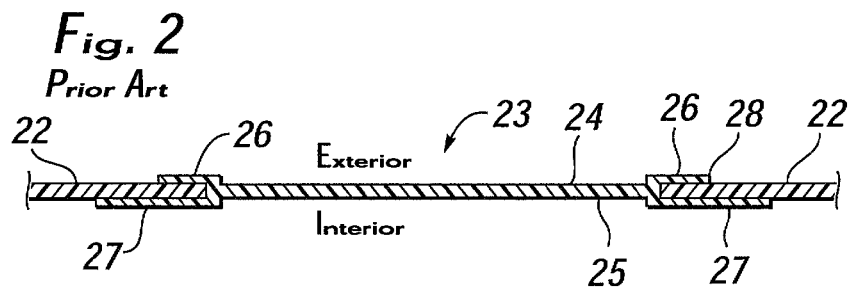
FIG. 2 is a cross-section, to a slightly enlarged scale, when viewed on section line 2-2 of the FIG. 1.

FIGS. 1 and 2 of the drawings illustrate a flexible implant construction of the prior art. A breast prosthesis 21 comprises a textured envelope or shell 22 formed by a conventional molding process on a mandrel. A patch 23 covers an aperture in the shell 22 formed during the mold process. As best seen in FIG. 2, the patch 23 comprises an external overlay 24 and an internal underlay 25, with respective overlapping portions 26, 27, so as to form a sandwich structure. The overlapping sections of the patch 23 and shell 22 as well as those portions of the overlay 24 and underlay 25 which are in contact are bonded together.

The patch can be bonded to the shell by a variety of means including chemical welding or bonding, ultrasonic welding, and heat/pressure fusing. One disadvantage of this process is that a ridge 28 is formed on the exterior as well as a concentric ring 29 formed by the bonding process, part or all of which may be smooth, i.e. where the textured exterior surface area of the shell 22 may be reduced by the overlap of the overlay 24. This is undesirable, because the exterior textured surface area ought to be maximized for surgical reasons. Moreover, the circular ring 29 and peripheral ridge 28 form a ridge on the breast prosthesis 21 that is discernible by feel after implantation. The peripheral portion 27 of the underlay 25 also presents a small internal ridge which is palpable after implantation. These physical discontinuities not only present unnatural tactile sensations, but may result in undesirable chafing between the prosthesis 21 and the breast cavity.

Figure 3:
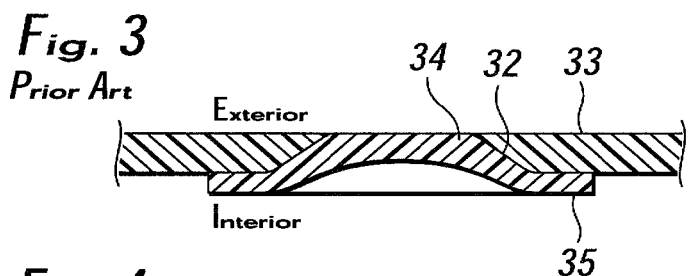
FIG. 3 shows, in cross-section, an alternative patch construction in accordance with the prior art with a chamfered edge of the aperture to be sealed by the patch.

FIG. 3 illustrates an implant shell 33 of the prior art having a chamfered edge 32 around the mold aperture and opening toward the interior of the shell. A patch member 34 bonded to the interior of the shell 33 includes a conical portion which fits closely against the chamfered edge 32 and a peripheral skirt 35 that abuts the interior of the shell 33. This construction eliminates an external ridge, such as at 28 in FIG. 2, but the peripheral skirt 35 still presents an interior ridge.

Figure 4:
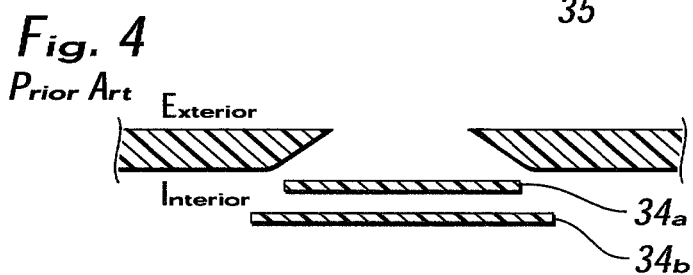
FIG. 4 shows, in cross-section, an alternative patch construction in accordance with the prior art.

Alternatively, as shown in FIG. 4, a patch applied from the interior of the shell 33 in FIG. 3 may comprise two parts, a cap plug portion 34a, slightly larger than the aperture, and an underlay portion 34b, larger still, such that when bonded together, the whole patch extends radially around the aperture in the same manner illustrated in FIG. 3.

The configurations shown in FIGS. 3 and 4 have the advantage that a stronger bond is formed between the edge of the aperture and the patch, since the edge area is increased by virtue of the chamfer 32, when compared to a squared edge, and that no ridge is formed on the exterior at the joint between the patch and the shell. However, as mentioned above, an interior ridge remains. It will be appreciated that the presence of any detectable seam between the patch and the shell represents a stress point which could possibly fail giving rise to leakage of fluid from the prosthesis, which must be avoided.

Figure 5:
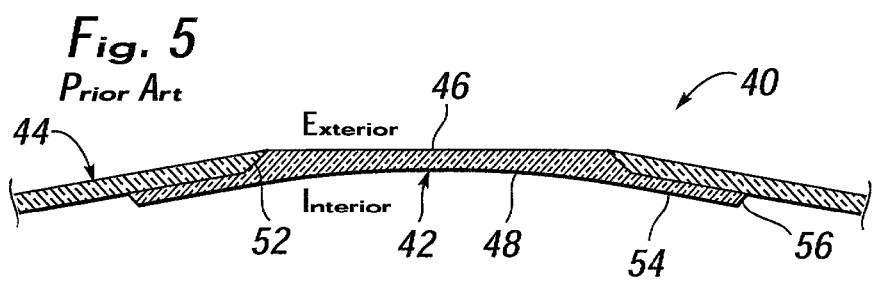
FIG. 5 shows, in cross-section, a still further alternative patch construction in accordance with the prior art.

Finally, FIG. 5 illustrates another patch configuration of the prior art in which a prosthesis 40 includes a patch 42 closing a mold aperture of a shell 44. The patch 42 comprises an external surface 46 visible through the aperture, and an internal surface 48. The aperture has a chamfered mouth 52 to which a peripheral extent of the external surface 46 conforms. The internal surface 48 extends outward from the mouth 52 in a skirt 54 that terminates at a peripheral edge 56. This patch configuration once again presents a smooth external surface to the prosthesis 40, with no ridge, and is somewhat more streamlined than earlier versions, but the internal peripheral edge 56 remains. Again, the edge 56 presents a relatively sudden surface step and stress point around the patch 42 that is discernible from outside the patient after implantation. In this context, a surface step is a relatively sudden surface change such as an increase or decrease in thickness at the shell wall/patch boundary.

Figure 6:
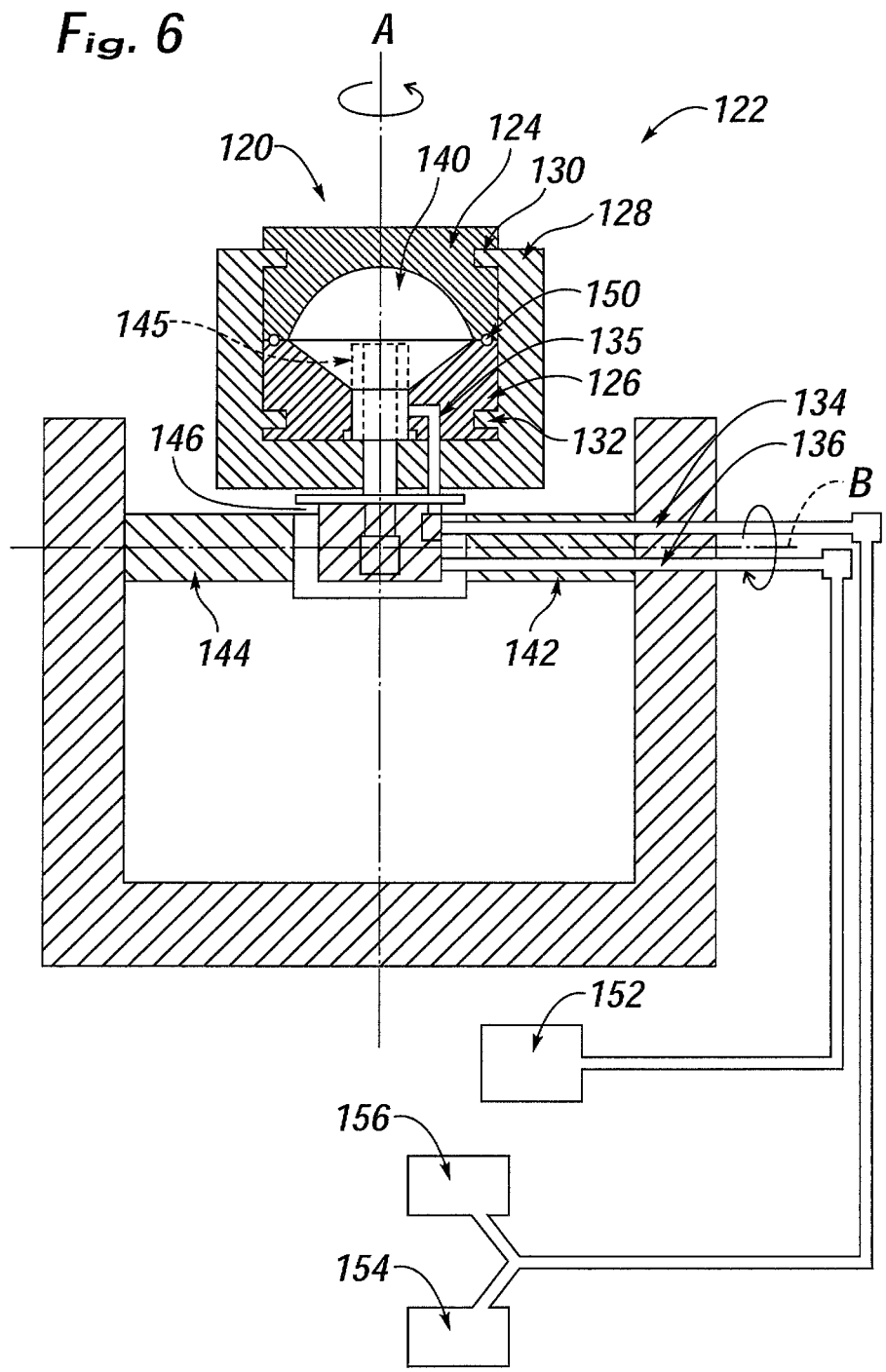
FIG. 6 is a schematic cross-section of an exemplary rotational molding system for use in forming the shell of a soft prosthetic implant of the present invention.

FIG. 6 is a schematic of an embodiment of a rotational molding system similar to that disclosed in Schuessler, U.S. Pat. No. 6,602,452, which can be used to form implant shells of the present invention. A two-piece case mold 120 affixes to a multi-axis rotational mold machine 122 by clamps securing top mold piece 124 and bottom mold piece 126 to clamp base 128 at top locking groove 130 and bottom locking groove 132, respectively. Vacuum connection 134 runs through one arm of the mold machine 122 to a vacuum opening 135. Material connection tube 136, through which silicone elastomer, liner materials, and/or air are injected into the mold cavity 140, may run through or along the same arm 142 as the vacuum connection 134 or by means of another arm 144. The input fluid then continues through a circular sprue tube 145 fitted in a circular opening (not numbered) of bottom mold piece 126. The sprue tube 145 defines a hollow bore that allows materials to enter an internal cavity of the two-piece case mold 120.

The hub 146 of the two arms rotates about axis A in the horizontal direction, while the arms 142, 144 rotate about axis B, which may be perpendicular to axis A. This allows a liner material or silicone elastomer material to uniformly coat the surface of the mold cavity 140. Two-piece case mold 120 may be manufactured from copper, aluminum, or other materials. The top mold piece 124 and bottom mold piece 126 fit together at their mating surfaces, seal with an O-ring 150, and then lock into clamp base 128 of multi-axis rotational molding machine 122.

Material reservoir 152 is fluidly coupled to connection tube 136 for providing silicone elastomer, liner material and/or air to cavity 140. Vacuum source 154 and solvent condenser 156 are fluidly coupled to vacuum connection 134. The hollow bore of the sprue tube 145 communicates with an inner vacuum tube (not shown) which in turn is connected to vacuum opening 135 and vacuum connection 134.

The rotational molding system of FIG. 6 has two distinct advantages over earlier methods for forming soft implant shells. First, the system includes a vacuum vent to the mold via a rotating arm of the equipment, which removes the solvent from silicones and other solvent-based or gas-emitting materials. A second advantage of the rotational molding system is that it enables the formation of articles without seams at the mold parting lines by first coating the inside of the mold with a thin layer of molding material such as polyethylene, polypropylene, nylon, fluoropolymer, polyester resin, polyurethane, epoxy or the like to create a mold liner. After the liner is cast, then the raw material, e.g. silicone elastomer, for the desired implant shell is injected into the mold cavity and similarly rotationally cast inside the liner, resulting in a temporary laminated construct. When the mold is disassembled and the construct is removed from the mold, the liner material and the implant are physically separated resulting in the desired article having a seamless configuration.

Figure 7:
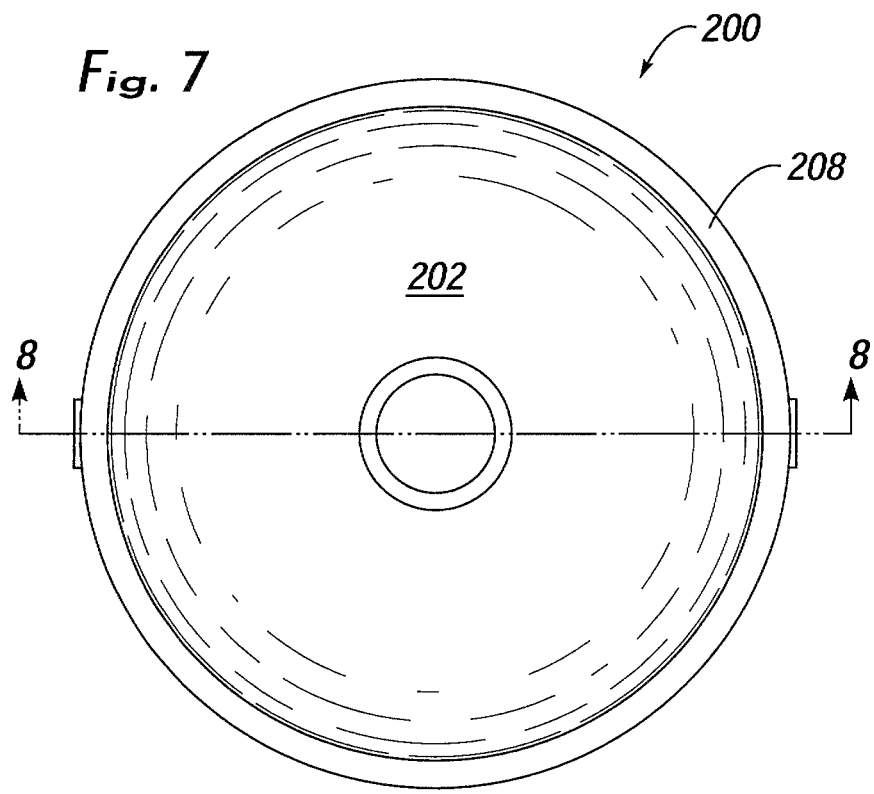
FIGS. 7 and 8 are bottom and sectional views of one embodiment of a mold for use in a rotational molding system such as shown in FIG. 6 to form an elastomeric implant that receives a flush patch of the present invention.
Figure 8:
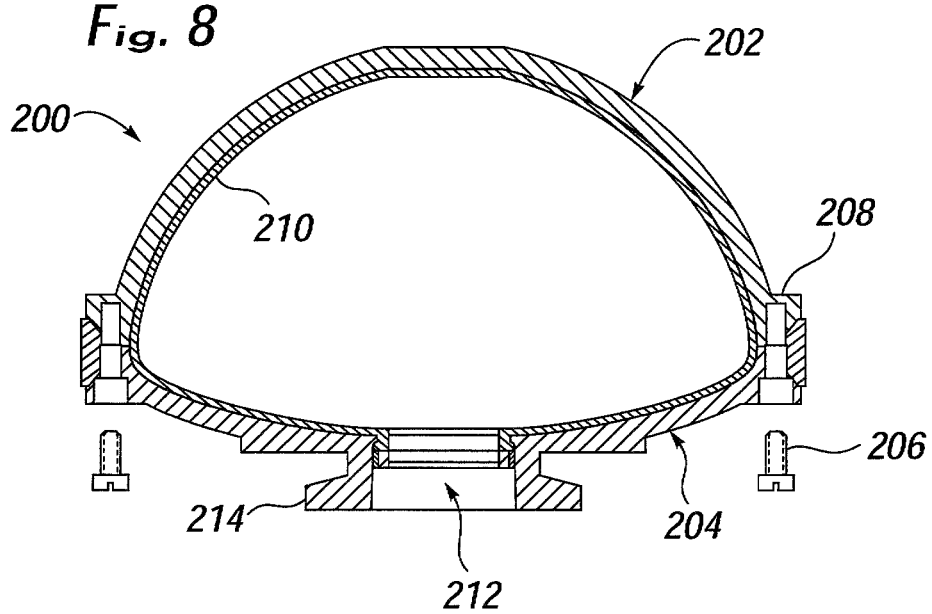

FIGS. 7 and 8 illustrate an alternative mold 200 for a rotational molding system, such as that described with reference to FIG. 6, which can be used to form implant shells of the present invention. As in the earlier embodiment, the mold 200 comprises a top mold piece 202 and bottom mold piece 204 held together by bolts 206 across respective flanges 208. An inner liner 210 is illustrated in cross-section in FIG. 8. Again, the presence of the inner liner 210 is a significant advantage because the implant shells may be formed without a seam that otherwise would result at the intersection of the two mold pieces 202, 204. Desirably, the mold pieces 202, 204 are formed of a metal such as aluminum, and the inner liner 210 is formed of a non-adherent material such as Teflon, for instance ETFE (ethylene-tetrafluoroethylene).

In contrast to the earlier-described embodiment, the inner liner 210 is intended to be reused every time a prosthetic implant shell is formed by the mold. The inner liner 210 remains within the cavity formed by the mold pieces 202, 204, and thus defines the inner surface of the mold 200, during the formation of a number of implants. Preferably the inner liner 210 may remain within the mold pieces 202, 204 for hundreds of uses. As with the earlier-described embodiment, the inner liner 210 is initially formed by rotational molding by injecting free-flowing liner material within the mold pieces 202, 204. The mold 200 functions much like the aforementioned two-piece case mold 120, in that it includes a relatively large circular opening 212 within a lower flange 214 through or into which inserts a sprue tube (such as the sprue tube 145 of FIG. 6).

FIG. 9 schematically illustrates an alternative single-piece mold 220 mounted on a rotational molding machine, such as described above, in the process of forming a soft implant 240 comprising an implant shell 244 having a molded-in patch 242, seen finished in FIG. 10. A single-piece mold 220 obviously eliminates any seam between mold parts, and thus a mold liner is unnecessary. After the implant shell 244 with the molded in-patch 242 is formed, the mold 220 is disengaged from the rotational molding machine leaving the patch visible through a mold neck 222. The resiliency of the material used for the patch and the shell enables them to be folded or otherwise compressed then removed from the mold neck 222.

The molding process involves introducing a silicone dispersion within the mold cavity, rotating the mold 220, and permitting a solvent within the silicone dispersion, such as xylene gas, to be evacuated through a vent tube that extends centrally through the patch 242. The silicone dispersion may be introduced straight into the mold through the patch while holding the patch 242 in place, such as with a spring (not shown), or another channel may be used for inserting the silicone. A mold plug contacts an external surface of the patch 242 and seals within the mold neck 222. The vent tube passes through a bore in the mold plug, and from there to a vacuum and solvent collection system.

FIG. 10 is a cross-sectional view through the exemplary gel-filled breast implant prosthesis 240 comprising the shell 244 and molded-in-place patch 242. The prosthesis 240 may be filled with a gel 246, such as silicone gel.

The patch 242 provides a reinforced access region on the surface of the prosthesis 240 for passage of one or more implements from the exterior to the interior. For instance, the mold process described above desirably utilizes the patch 242 as a reinforced conduit through which both the silicone dispersion tube inserts, as well as the vent tube as shown in FIG. 9. Subsequent to the shell molding process, a third tube may be inserted through the patch to fill the interior of the shell with a silicone gel. And of course a primary function of the patch 242, as detailed herein, is to enable formation of a totally seamless implant with no surface steps inside or out.

Figure 11A:
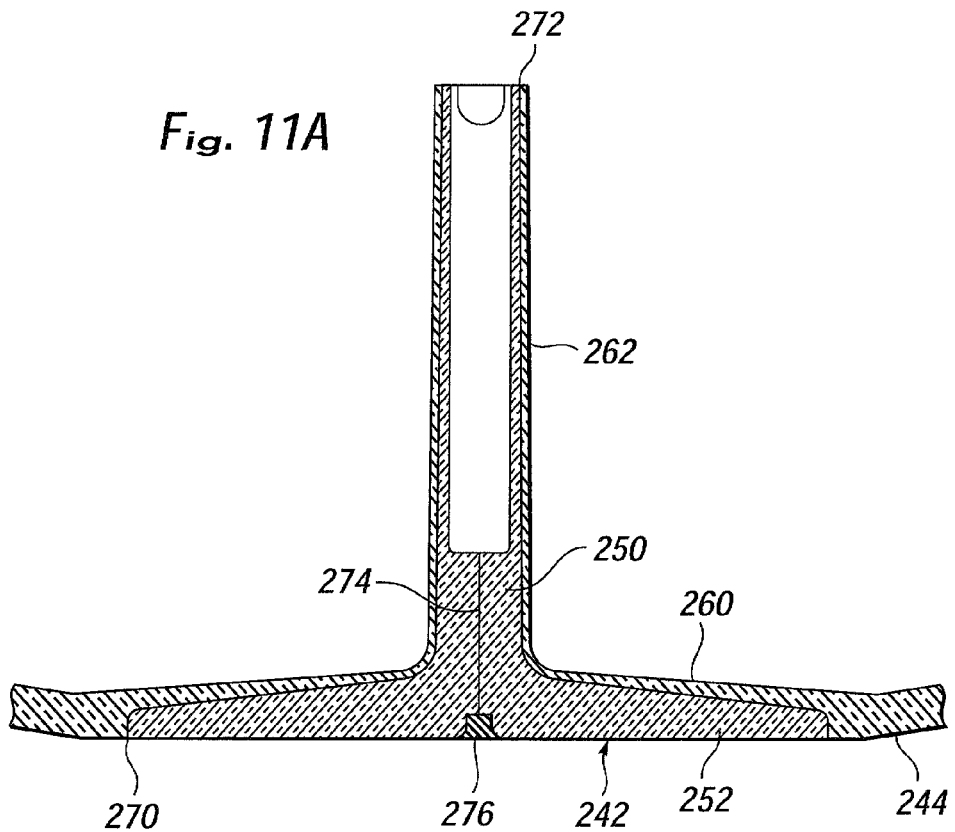
FIG. 11A is a detailed view of the interface between the flush patch and the shell of the breast implant prosthesis of FIG. 10.

FIG. 11A is a detailed view of the interface between the patch 242 and the shell 244. The patch 242 includes a stem 250 projecting directly radially into the interior of the shell 244 and an outward flange 252 generally conforming to and forming a continuation of the exterior shape of the shell 244. The material of the shell 244 extends over the internal surface of the flange 252 at ring 260, extending at least to the stem 250, and preferably continues in a tube 262 around the stem 250. Because the patch flange 252 increases in radial thickness from its periphery toward its center, the wall thickness of the ring 260 tapers thinner from the main part of the shell 244 to the tube 262, and preferably has a uniform thickness along the stem 250. By virtue of the implant material extending therearound, the patch 242 is securely held in place.

By introducing the patch 242 during the process of molding the shell 244, rather than applying the patch to the shell aperture afterwards, the patch integrates with the casting material flowing over and around, thus producing a flush surface both inside and out. In particular, an external surface of the prosthesis including a circular interface line 270 at a flush butt joint between the patch 242 and shell 244 has no ridges or other surface irregularities. A butt joint means the juxtaposition of two edges, in this case an inner-facing edge of the shell 244 and the peripheral edge of the patch 242. The absence of surface interruptions is a great advantage in reducing irritation to tissue surrounding the implanted prosthesis, which has been traumatized and is susceptible to inflammation. Likewise, an internal surface of the prosthesis in the area of the patch 242 has no surface irregularities, and in particular the boundary between the patch 242 and shell 244 is relocated to the radially inner end 272 of the stem 250. Furthermore, molding the patch 242 into the shell 244 eliminates a secondary manufacturing step of adhering a patch to the shell.

It is important to note that while prior implants utilized a patch to cover an aperture left over as an artifact of the mold process, the shell 244 actually has no such aperture. More accurately, the shell 244 has a contiguous and consistent wall except in an access region across which the patch 242 extends. That is, the access region interrupts the generally constant thickness shell wall. The patch 242 provides an access medium or port through which tubes or other instruments may be inserted into the inner cavity of the shell 244. In the access region, the material of the shell thins to form the ring 260 over the internal surface of the flange 252 and the tube 262 around the stem 250. Because the material of the shell 244 does not cover the open top of the stem 250, an aperture through the shell technically exists, though not the same type of aperture as previously seen with prior art shells. Indeed, in an alternative version in FIG. 11B the shell may not even have an aperture, and the patch in that case does not cover anything but rather parallels, supports, or is juxtaposed against the thinned access region to provide the access port. In this sense, therefore, the term "patch" is sort of a misnomer, but will be retained for the sake of familiarity.

The stem 250 of the patch 242 may be utilized to help prevent clogging of tubes inserted into the cavity of the mold. For example, as seen in FIG. 9, a vent tube extends through a channel 274 (FIG. 11A) in the patch 242 and extends into the mold cavity through the inner end 272 of the stem 250. The silicone dispersion that may at times aggregate near the patch 242 is prevented from entering and potentially clogging the vent tube by virtue of imposition of the upstanding stem 250. The channel 274 also provides an avenue through which a gel-filling tube (not shown) may be introduced after the shell 244 and patch 242 are molded together. For instance, a gel, such as silicone gel 246 shown in FIG. 10, may be injected through a tube inserted through the channel 274. Therefore, the channel 274 may be used for introducing silicone to the mold to form the shell, for venting the mold cavity during the mold process, and/or for introducing the silicone gel into the hollow prosthesis. Instead of providing a pre-formed channel 274, the patch 242 may be made of a material or be configured to be self-sealing. However, given the relatively large bore tubes that may pass through the patch, a channel that is subsequently sealed is more practical. A small well at the opening of the channel 274 that helps guide the vent and gel fill tubes into the channel may be filled with a silicone plug 276, such as a silicone adhesive, to form a completely even outer prosthesis surface.

Figure 11B:
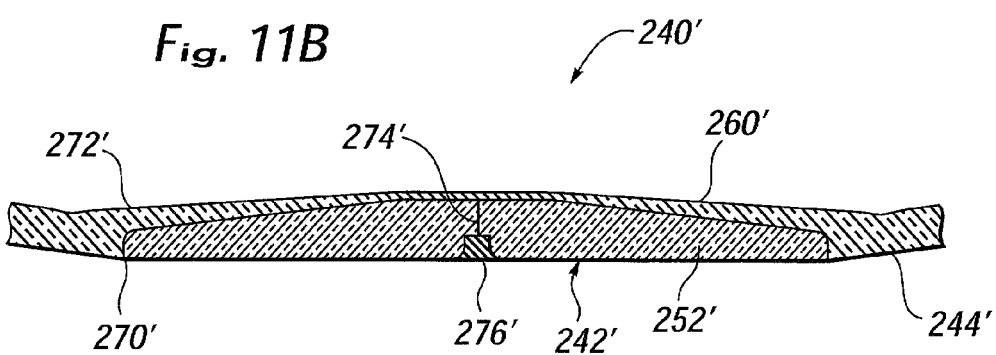
FIG. 11B is a detailed view of the interface between an alternative flush patch and the shell of the breast implant prosthesis of FIG. 10.

FIG. 11B illustrates a portion of a soft implant prosthesis 240' that incorporates a low-profile flush patch 242'. The patch 242' includes an outwardly extending flange 252' but differs from the above-described patch 242 by eliminating the radially extending stem, and instead has a substantially flat disk shape. The patch 242' molds in place so that the surrounding shell 244' again meets flush in a butt joint with the outward flange 252' to form a smooth exterior surface interface 270'. The material of the shell 244' also flows over the inner face of the patch 242' to form a cap 260' that completely eliminates any internal boundary between the patch and shell. The region 272' of the shell 244' adjacent and inward with respect to the outer edge of the patch flange 252' is smooth, and the thickness of the shell 244' at that point entirely covers and cushions any potential tactile discontinuity presented by the edge of the flange. There are certainly no sudden surface steps inside and outside the patch periphery, as in the prior art. A self-closing channel 274' through the patch 242' again provides passage for insertion of a vent or gel fill tube, and a small plug 276' fills a small well at the outlet of the channel after formation of the implant 240'.

It is contemplated by the inventors that a fill valve can be provided in the patch for facilitating inflation and deflation of the implant shell. For example, the implant may be an intragastric balloon and the patch may include a valve useful for both inflating and deflating the balloon. In other embodiments of the invention, the implant may be a saline fillable breast implant or a tissue expander and the patch may include a suitable valve for enabling filling and/or draining of the implant. All of these are considered to fall within the scope of the present invention.

For breast implants, the formed shell is ready for further assembly or processing consistent with the usual manner in creating a final breast implant product. For example, the implant shell is filled with a filler material of silicone gel or other biocompatible gel material well known to those of skill in the art, such as gel 246 shown in FIG. 10.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method of formation of a medical implant, comprising:
   providing a mold cavity having a sprue orifice;
   providing a patch including a hollow stem and an outer flange having a peripheral edge;
   covering the sprue orifice with the patch such that the stem projects radially into the mold cavity;
   introducing a silicone elastomer into the mold cavity through the stem of the patch;
   causing the silicone elastomer to distribute generally evenly around the mold cavity and over at least a portion of the patch;
   curing the silicone elastomer to form a hollow implant shell having the patch molded thereto, the stem projecting radially inwardly into the interior of the shell, and the shell forming a flush butt joint against the peripheral edge of the flange, overlapping an inner surface of the flange and extending at least to the stem; and
   removing the implant shell having the patch molded thereto from the mold cavity.

2. The method of claim 1, wherein during the step of causing the silicone elastomer to distribute generally evenly around the mold cavity the method further includes extending a vent tube through the patch and venting gas from within the mold cavity though the vent tube.

3. The method of claim 1 wherein the flange of the patch increases in radial thickness from the peripheral edge toward the stem.

4. A method of making a breast implant, comprising:
   providing a mold cavity having a sprue orifice;
   providing a patch including a hollow stem and an outer flange having a peripheral edge;
   covering the sprue orifice with the patch such that the stem projects radially into the mold cavity;
   introducing a silicone elastomer into the mold cavity through the stem of the patch;
   causing the silicone elastomer to distribute generally evenly around the mold cavity and over at least a portion of the patch;
   curing the silicone elastomer to form a hollow breast implant shell having the patch molded thereto, the stem projecting radially inwardly into the interior of the shell, and the shell forming a flush butt joint against the peripheral edge of the flange, overlapping an inner surface of the flange and extending at least to the stem; and
   removing the hollow breast implant shell having the patch molded thereto from the mold cavity.

* * * * *

UNITED STATES PATENT AND TRADEMARK OFFICE
CERTIFICATE OF CORRECTION

| | | |
|---|---|---|
| PATENT NO. | : 8,609,004 B2 | Page 1 of 1 |
| APPLICATION NO. | : 13/288885 | |
| DATED | : December 17, 2013 | |
| INVENTOR(S) | : David J. Schuessler et al. | |

It is certified that error appears in the above-identified patent and that said Letters Patent is hereby corrected as shown below:

In the Specification

In column 2, line 43, delete "finable" and insert -- fillable --, therefor.

Signed and Sealed this
Twenty-sixth Day of May, 2015

Michelle K. Lee
*Director of the United States Patent and Trademark Office*